United States Patent
Rhodes et al.

(10) Patent No.: US 6,767,443 B2
(45) Date of Patent: Jul. 27, 2004

(54) METHOD AND APPARATUS FOR ELECTROPHORETIC FOCUSING

(76) Inventors: Percy H. Rhodes, 412 Westburg Ave., Huntsville, AL (US) 35801; Robert S. Snyder, 1515 Monte Sono Blvd., Huntsville, AL (US) 35801

( * ) Notice: Subject to any disclaimer, the term of this patent is extended or adjusted under 35 U.S.C. 154(b) by 457 days.

(21) Appl. No.: 09/884,139

(22) Filed: Jun. 20, 2001

(65) Prior Publication Data

US 2002/0008027 A1 Jan. 24, 2002

Related U.S. Application Data

(60) Continuation-in-part of application No. 09/788,458, filed on Feb. 21, 2001, which is a continuation-in-part of application No. 09/730,834, filed on Dec. 7, 2000, now Pat. No. 6,478,942, which is a division of application No. 09/277,944, filed on Mar. 29, 1999, now Pat. No. 6,171,466.

(51) Int. Cl.[7] .............................................. G01N 27/447
(52) U.S. Cl. ...................................... 204/465; 204/459
(58) Field of Search ................................. 204/459, 450, 204/465, 518, 600, 615, 644, 666, 670, 671; 210/748

(56) References Cited

U.S. PATENT DOCUMENTS

| | | |
|---|---|---|
| 3,149,060 A | 9/1964 | Dobry et al. |
| 3,412,008 A | 11/1968 | Strickler |
| 4,309,268 A | 1/1982 | Richman |
| 4,362,612 A | 12/1982 | Bier |
| 4,588,492 A | 5/1986 | Bier |
| 4,752,372 A | 6/1988 | Rhodes et al. |
| 5,336,387 A | 8/1994 | Egen et al. |

OTHER PUBLICATIONS

Rhodes et al., "Electrohydrodynamic Distortion of Sample Streams in Continuous Flow Electrophoresis", Journal of Colloid and Interface Science, vol. 129, No. 2, Apr. 1989, pp. 78–90.

Ivory et al., "Continuous Counteracting Chromatographic Electrophoresis", Biotechnol. Prog. 1980, 6, 21–32.

Primary Examiner—Alex Noguerola
(74) Attorney, Agent, or Firm—Stites & Harbison PLLC; B. Aaron Schulman

(57) ABSTRACT

An apparatus and method is described for obtaining a preparative-scale, free-fluid electrophoretic separator with high resolution as well as an analytical capability commensurate with capillary zone electrophoresis. The electrophoretic focusing apparatus and method of the present invention features a separation chamber bounded by planar precision-pore, insulated screens, a plurality of purge chambers, a plurality of electrode chambers, and a plurality of pump means. The separation device of the invention is capable of high speed of separation and short residency of sample through the use of high voltage gradients which are produced by relatively low voltages applied across the narrow chamber dimensions. The present apparatus and method thus achieves high resolution of separation in an analytical or a preparative mode through a practically unlimited scale-up potential, and controls the adverse effects of Joule heating and electrohydrodynamics on the electrophoretic separation procedure.

14 Claims, 2 Drawing Sheets

METHOD AND APPARATUS FOR ELECTROPHORETIC FOCUSING

This application is a continuation-in-part of U.S. patent application Ser. No. 09/788,458, filed Feb. 21, 2001, which was a continuation-in-part of U.S. patent application Ser. No. 09/730,834, filed Dec. 7, 2000, now U.S. Pat. No. 6,478,942 B2, which was a divisional application of U.S. patent application Ser. No. 09/277,944, filed Mar. 29, 1999, now U.S. Pat. No. 6,171,466.

FIELD OF THE INVENTION

The invention relates in general to an apparatus and method for achieving electrophoretic focusing, and in particular to an apparatus for achieving electrophoretic separation and purification which is characterized by a separation chamber formed between two precision-pore, insulated screens and which also includes inlet and outlet ports, a plurality of purge chambers for extracting extraneous fractions and for providing thermal cooling, a plurality of electrodes to provide a transverse electric field in the separation chamber, and pumping means for pumping sample, carrier buffer, purge buffer and electrode rinse buffer through the apparatus, and a method of employing this apparatus to achieve separation and collection of a desired component from a biological or chemical sample.

BACKGROUND OF THE INVENTION

There are two electrokinetic methods that have had success separating biological materials, namely, zone electrophoresis and isoelectric focusing. Electrophoresis is the movement of suspended or dissolved charged particles in response to an applied electric field. The rate of motion depends upon the charge, size and shape of the particles and specific properties of the solvent buffer and its container. In zone electrophoresis, the components in a short sample zone are separated by the action of the electric field. The injection of a narrow, uniform zone and the absence of dispersive fluid flows are necessary conditions for successful operation. Significant sources of dispersion are: 1) uneven (parabolic) flows; 2) electrohydrodynamic flows; 3) molecular diffusion; 4) thermal convection; 5) sedimentation; 6) thermally induced sample mobility variations; and 7) electroosmosis.

In continuous zone electrophoresis (CFE), the electrolyte solution flows in a direction perpendicular to the electric field and the mixture to be separated is inserted continuously into the flowing solution. Components of the mixture are deflected according to their electrophoretic mobilities and can be collected continuously in a finite array of collection ports after their migration. Svensson and Braftsten were the first to report a method for carrying out electrophoresis continuously. They used a lateral electric field in a narrow Plexiglas box packed with glass powder as an anti-convective medium. Durrum modified the above configuration by replacing the glass-filled box with a filter paper curtain, hanging in a free vapor space. While both of these methods demonstrated continuous electrophoresis, they both used a stabilizing medium. Anti-convective media cause many problems such as reduction of the flow capacity by their presence, electroosmosis in the interstices, adsorption of the sample and "packing or eddy diffusion". Efforts were then made to do continuous electrophoresis in a free fluid. Dobry and Finn (U.S. Pat. No. 3,149,060) were the first to report continuous flow free fluid electrophoresis in a rectangular chamber with a cross-section of low aspect ratio, hence providing little resistance to thermal convective flow disturbances. This configuration was limited to very low electric fields and required the use of buffer thickening agents to suppress convective eddies. Philpot described a continuous flow electrophoresis system with the electric field applied across (perpendicular to) a thin film of liquid. He later wrapped his thin film geometry into a thin annulus surrounded by two concentric cylinders (electrodes). The outer cylinder rotated to provide a stabilizing velocity gradient.

Mel in 1959 reported the first use of a high aspect ratio rectangular separation chamber using a lateral electric field. The "thin" chamber of 0.7 cm thickness provided the necessary wall interaction to suppress thermal convective flows to the extent that a less viscous free flow buffer could be used. This design served as the impetus for the development of the conventional CFE machines of the 60's and 70's with their chamber cross-section of high aspect ratio and laterally directed electric fields. During this time frame, Hannig and his co-workers developed CFE by making the chamber cross-sections even thinner, approaching 0.25 cm for some designs. Unfortunately, the gains made in suppressing thermal convection were wiped out by electrohydrodynamic interaction with intrinsic chamber fluid flows to cause crescent-shaped distortions. Nevertheless, a variety of CFE instruments were manufactured according to the designs of Hannig (in Germany) and Strickler (in the US) (U.S. Pat. No. 3,412,008) and several hundred instruments were used in laboratories around the world. Rhodes and Snyder subsequently devised a technique to minimize these flow distortions (U.S. Pat. No. 4,752,372).

While the concept of using a counter flow to oppose the electrophoretic migration velocity has long been considered an attractive means to achieve a focusing effect, no method has been found to provide the uniform velocity field necessary to bring this concept to fruition. Richman patented a counter-flow method where axial bands of electroosmotic coatings of varying zeta potential would "straighten" distorted sample bands (U.S. Pat. No. 4,309,268). The method was impractical because most coatings change with time and there exists no spectrum of coatings with respect to zeta potential. A more practical approach that did not use counter-flow was suggested by Strickler wherein the CFE was divided into two vertical compartments, each with a different wall coating, so that the combined electroosmotic flow would yield a more coherent sample band. Subsequently, Ivory used counter-flow to increase sample residence time in a recycling CFE. Egen, et al. have also devised a counterflow gradient focusing method (U.S. Pat. No. 5,336,387).

While the crescent phenomenon was long known to cause untenable sample stream distortion in CFE instruments, it was not until 1989 that Rhodes and Snyder showed that electrohydrodynamics transforms initially circular sample streams into ribbons that initiate the crescent shaped distortions. The operation of CFE devices was labor intensive and unreliable due to contamination of the closely spaced chamber walls and the resultant electroosmotic flow variations through the chamber.

Isoelectric focusing (IEF) is an electrophoretic technique that adds a pH gradient to the buffer solution and together with the electric field focuses most biological materials that are amphoteric. Amphoteric biomaterials such as proteins, peptides, nucleic acids, viruses, and some living cells are positively charged in acidic media and negatively charged in basic media. During IEF, these materials migrate in the pre-established pH gradient to their isoelectric point where they have no net charge and form stable, narrow zones. In spite of the very long time required for isoelectric focusing, this process yields high resolution bands because any amphoteric biomaterial which moves away from its isoelectric point due to diffusion or fluid movement will be returned by the combined action of the pH gradient and electric field. The focusing process thus purifies and concentrates sample into bands that are relatively stable. This is a powerful concept that has yielded some of the highest resolution separations, especially when coupled with electrophoresis in two-dimensional gels.

IEF had its practical beginning in the mid-1950's when Kolin first demonstrated the concept of focusing ions in a pH gradient by placing a molecular sample between an acidic and a basic buffer and applying an electric field. Although the constituents focused rapidly, the gradient soon deteriorated due to the concurrent electrophoretic migration of all of the buffering ions. The synthesis of stable carrier ampholytes by Vesterberg and their successful commercial development led to broad use in gels or other restrictive media to suppress electroosmosis and thermal convection during analytical separations.

The high resolution achieved by IEF encouraged many attempts to develop a preparative version of the process. This proved to be much more difficult for IEF than zone electrophoresis because of the variable fluid properties and sample characteristics within the chamber leading to changing values of electroosmosis and thermal convection during the separation. Various CFE devices were modified to run with an amphoteric mixture instead of buffer but the problems (long focusing time requiring a slow flow through the chamber, pH drift toward the cathode, reduced voltage/current levels for acceptable heating and convection) became insurmountable. Bier developed an external cooling system, added sensors and demonstrated the improved focusing with recycling (U.S. Pat. No. 4,362,612). Bier then added a stabilizing assembly rotation to the membrane segmentation and a novel collection system (U.S. Pat No. 4,588,492) which led to the Roto-Phor from Bio-Rad (Hercules, Calif.).

Unfortunately there are drawbacks to IEF that have limited its applications. The rate of electrophoretic migration of each charged species decreases progressively as it approaches its isoelectric point and long residence times are required for high resolution. Proteins have reduced solubility at their isoelectric point although precipitation of the concentrated bands can be minimized by addition of detergent. Additional problems relate to the commercial amphoteric solutions, including: 1) difficulty of extracting the separated proteins, peptides, etc., from the amphoteric solutions because of their similar physical properties and interactions; 2) chemical toxicity; 3) handling problems; and 4) cost. IEF has also been hindered by problems during the transition from an analytical system to a preparative system that have limited its intended use. It is thus highly desirable to develop a focusing system for separating biological molecules and other components in a mixture which is able to avoid all of the problems of the prior art and which can achieve high resolution of separation in an analytical or a preparative mode through a practically unlimited scale-up potential. It is also highly desirable to develop an electrophoretic focusing system which can control the adverse effects of Joule heating and electrohydrodynamics on the electrophoretic separation procedure.

SUMMARY OF THE INVENTION

It is an object of the present invention to provide a preparative-scale free-fluid electrophoretic separator with high resolution as well as an analytical capability commensurate with capillary zone electrophoresis. The particular mode of high-resolution separation as provided by the present invention, which is referred to as electrophoretic focusing, combines features of electrophoresis and isoelectric focusing to accomplish large scale purifications and fractionations that have not been possible before now.

Many research and applications tasks with biological materials require a large source of highly purified biologically active molecules. The diverse supply of materials for biotechnology ranging from plants to genetically derived sources are placing increased demands on separation and purification. Existing preparative separation techniques yield products with a variety of impurities that can be measured analytically but not removed. Analytical techniques have been perfected in recent years but attempts to scale these techniques into larger production have relied on generally increasing the physical dimensions instead of investigating a new technique. It is an advantage of the focusing device of the present invention that it will be able to purify biological materials in amounts and to purity levels above those now obtainable.

In accordance with the present invention, there is provided an electrophoretic focusing apparatus and method which is useful in achieving the separation and purification of particular components of a mixture of biological or chemical materials. The general purpose of the invention is a continuous processing system that separates and purifies any soluble or microparticulate sample that acquires a surface electric charge when immersed in a polar (e.g. aqueous) fluid environment. It combines the best features of electrophoresis and isoelectric focusing in a novel device that incorporates a combination of transverse electric field and buffer flow field to focus and collect any selected biological component. Although the high resolution achievable by focusing is familiar to isoelectric focusing, electrophoretic focusing avoids many of its problems, such as the need for complex buffers and the long times required for the molecules to reach their isoelectric point. This new concept incorporates a large-gap chamber and control of all sources of sample dispersion. The design of the electrophoretic focusing chamber combined with the orientation and magnitude of the electric fields and buffer flows are planned to eliminate sample dispersion. The large gap will keep sample away from the walls as well as increase its throughput.

It is another object of the present invention to develop a separation device capable of high speed and short residency through the use of high voltage gradients. These high voltage gradients are produced by relatively low voltages applied across the narrow chamber dimensions. The goal of high resolution of separation can be achieved through the use of the present invention in an analytical or a preparative mode through a practically unlimited scale-up potential. A further goal is to control the adverse effects of Joule heating and electrohydrodynamics.

These and other objects and benefits are achieved by the use of the present invention which provides a number of innovations and insights with regard to fundamental fluid and thermal geometries and operations. The focusing is accomplished with a minimum of sample migration which leads to a higher resolution in a shorter time. Adiabatic thermal conditions in the lateral (scale-up) dimension permit a large increase in throughput at no apparent loss of resolution. Active cooling limits the maximum chamber temperature and its relationship to the chamber orientation and buffer fluid transport is such as to limit thermal convection. Porous, rigid screens permit a controlled focusing cross-flow which balances the electrophoretically-driven sample velocity. In the preferred method in accordance with the invention, separation and collection of at least one component from a mixture of components is obtained by the steps of (a) providing an apparatus comprising a separation chamber and a plurality of purge chambers, and establishing a first buffer flow in the separation chamber in the axial direction, said first buffer flow having a first flow rate; (b) establishing a second buffer flow in the separation chamber consisting of two flows on either side of the first flow that converge on the first flow at the chamber entrance and diverge from the first flow at the chamber exit; (c) establishing a third buffer flow in each of at least two purge chambers in the axial direction, said second buffer flow having a second flow rate, said second buffer fluid flow having a second flow rate higher than that of the first flow rate; (d) introducing two precision-pore screens that partition the said separation chamber from each of the two said purge chambers; (e) establishing a fourth buffer flow by the biasing of the purge valves to control said fourth buffer flow from one of the purge chambers through a precision-pore screen transversely into the separation chamber, then out of the separation chamber through the second precision-pore screen into a second purge chamber, thus providing the required uniform focusing fluid velocity in the separation chamber; (f) introducing the mixture of sample components with the said first buffer flow directly into the separation chamber flow entrance or through at least one injection port located in the separation chamber interior; (g) controlling the second buffer flow to converge and thin the first buffer flow with sample components at the separation chamber entrance and then diverge and extract sample components at the separation chamber exit; and (h) applying an electrical potential transversely across the separation chamber in the form of a constant voltage gradient to impart electrophoretic velocity to the fractional components in the separation chamber in the transverse direction perpendicular to the first buffer flow direction and parallel to the fourth buffer flow direction.

DETAILED DESCRIPTION OF THE PREFERRED EMBODIMENTS

Figure 1:
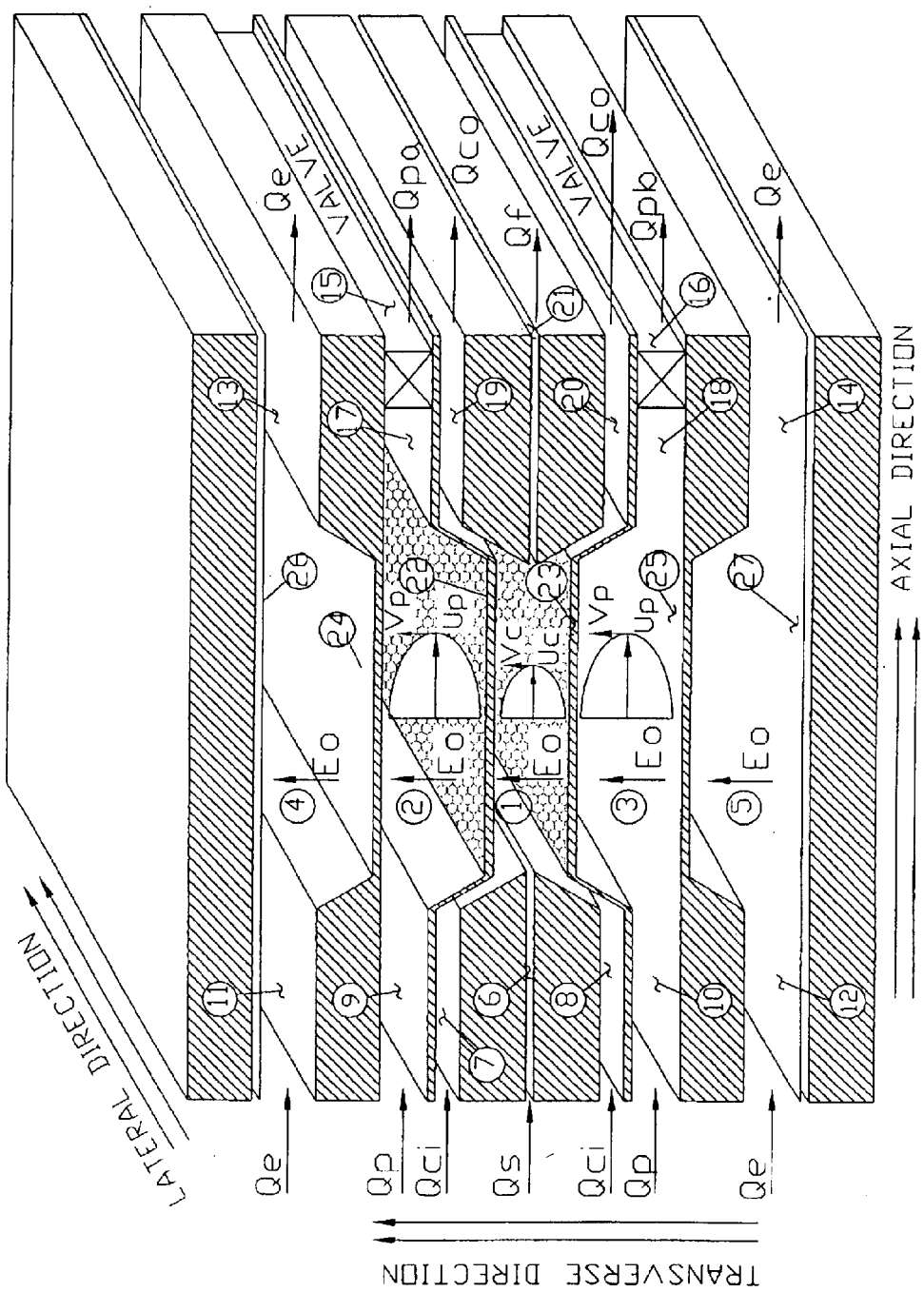
FIG. 1 is a schematic view of the analytical configuration of the present invention, taken in the axial, transverse and lateral directions.

The detailed description of the preferred embodiments below is to be taken in conjunction with the drawing figures as described above wherein like numerals represent the same elements in the different figures. In addition, the disclosures of the parent applications of the present application as set forth above are considered part of the present specification and are incorporated by reference as if set forth in full herein.

The principle of electrophoretic focusing utilized in conjunction with the present invention consists of opposing the electrophoretic sample velocity with a uniform fluid flow transverse to the direction of carrier flow through the chamber. The uniqueness of this invention is how this principle is used in conjunction with a constant voltage field to achieve a novel and powerful method of continuous sample separation. This result is achieved by using a uniform cross-flow in opposition to an electric field to confine, or focus, a particular fraction in the separation chamber.

If the electric field is configured in the transverse direction (instead of the lateral direction as with CFE), electroosmotic flow becomes negligible and the viscous parabolic flow is orthogonal to the migration direction and hence also ceases to be a factor. Since the transverse migration is now in the narrow chamber dimension, the sample residence time is quite short and normally resolution will suffer. However, if a cross-flow is used, the sample will be held in the chamber by the cross-flow, thus improving the resolution by some calculable amount. This solution to the problems of CFE has been considered by past inventors but the problem of obtaining a uniform cross-flow combined with an area electrode associated with the broad chamber wall has kept this idea from realization. As the details of the invention show, this problem is solved by a unique utilization of micro-pore, thin, rigid, insulating screens.

The electrophoretic separator of the present invention is primarily characterized by a separation chamber formed between two precision-pore insulated screens. The perforations permit transverse fluid flow through the chamber to effect a separation of one or multiple species and also to provide cooling in the chamber interior. This unique use of cross-flow focuses one sample fraction continuously in the chamber when using a constant electric field to oppose the cross-flow. Since the separation is carried out in the direction transverse to the carrier buffer flow, the focusing is accomplished with a minimum of sample migration which leads to a higher resolution in a shorter time. The relatively short transverse dimension allows the use of a high voltage gradient derived from a low source voltage. When high resolution is desired, i.e., analytical separations, the sample is injected and collected in singular injection and collection ports so that the chamber is only partially filled with sample. When high throughput i.e., preparative separations are desired, the sample fills the entire chamber. This latter configuration provides a homogeneous medium between the chamber walls and eliminates conductivity gradients which produce destructive circulatory flows through Joule heating and electrohydrodynamics.

Another problem with existing continuous flow devices is the method of sample collection. The separated fractions must be collected by a finite number of collection ports which ultimately limit resolution. Collection for a batch process, such as chromatography or capillary electrophoresis, poses no such problem as each separate fraction can be individually collected over a variable time interval rather than a limited fixed distance interval between each adjacent collection port. This invention can collect fractions as a function of time by varying the cross-flow velocity to produce a histogram similar to that obtained from chromatography or capillary electrophoresis.

In the preferred embodiment of the present invention, separation and collection of at least one component from a mixture of components is obtained by the steps of (a) providing an apparatus comprising a separation chamber and a plurality of purge chambers, and establishing a first buffer flow in the separation chamber in the axial direction, said first buffer flow having a first flow rate; (b) establishing a second buffer flow in the separation chamber consisting of two flows on either side of the first flow that converge on the first flow at the chamber entrance and diverge from the first flow at the chamber exit; (c) establishing a third buffer flow in each of at least two purge chambers in the axial direction, said second buffer flow having a second flow rate, said second buffer fluid flow having a second flow rate higher than that of the first flow rate; (d) introducing two precision-pore screens that partition the said separation chamber from each of the two said purge chambers; (e) establishing a fourth buffer flow by the biasing of the purge valves to control said fourth buffer flow from one of the purge chambers through a precision-pore screen transversely into the separation chamber, then out of the separation chamber through the second precision-pore screen into a second purge chamber, thus providing the required uniform focusing fluid velocity in the separation chamber; (f) introducing the mixture of sample components with the said first buffer flow directly into the separation chamber flow entrance or through at least one injection port located in the separation chamber interior; (g) controlling the second buffer flow to converge and thin the first buffer flow with sample components at the separation chamber entrance and then diverge and extract sample components at the separation chamber exit; and (h) applying an electrical potential transversely across the separation chamber in the form of a constant voltage gradient to impart electrophoretic velocity to the fractional components in the separation chamber in the transverse direction perpendicular to the first buffer flow direction and parallel to the fourth buffer flow direction.

In addition, further information regarding the preferred method of the present invention is provided in the following description of the Analytical Configuration and Preparative Configuration modes of the invention.

I. Analytical Configuration

FIG. 1 shows the three-dimensional chamber in its analytical configuration with the different flows and flow regions. The chamber is comprised of a plurality of flow regions or sub-chambers, such as the five elements 1, 2, 3, 4 and 5. In the preferred embodiment, the separation chamber 1 is bounded by two fine mesh, precision pore, insulated screens 22 and 23. Carrier buffer Qci enters the chamber through ports 7 and 8 while sample Qs is injected through port 6. The converging flows in the vicinity of the injection point are significant as will be discussed later. The buffer and injected sample lamina flow through the chamber as shown with center plane velocity Uc. The focused sample fraction Qf exits the chamber through port 21 while the carrier buffer Qco exits through ports 19 and 20.

As shown in FIG. 1, the separation chamber 1 is flanked by two purge chambers 2 and 3. The purge flows Qp enter through ports 9 and 10 and cause a velocity profile Up in the purge chambers. The purge flows exit through ports 17 and 18 and through purge valve A, 15 and purge valve B, 16. The relative purge valve openings set the purge flow out Qpa and Qpb and thus regulate the amount of cross-flow in the separation chamber which will be discussed in detail later. An electric field Eo is impressed in the separation chamber 1 by electrodes 26 and 27. These electrodes are located in the electrode chambers 4 and 5, respectively. Rinse flows Qe enter the chamber through ports 11 and 12 to expel electrolysis products through ports 13 and 14. Membranes 24 and 25 isolate the electrode chambers from electrolysis gas and products while allowing current flow to maintain the electric field.

If the upper electrode 26 is negative and the bottom electrode is positive, an electric field Eo exists in the separation chamber 1 which will cause a negatively charged sample to migrate down (negative transverse direction) against the uniform transverse focusing velocity Vc as determined by the relative settings of the purge valves 15 and 16. Consider a sample fraction of electrophoretic mobility $\mu_i$=Vc/Eo that has been injected through the injection port 6 located at the separation chamber center plane. The sample fraction $\mu_i$ will remain in the vicinity of the center plane of the separation chamber 1 and move through it with a carrier buffer velocity Uc and be collected at the collection port 21. All other sample (mobility different than $\mu_i$) will either exit through ports 19 and 20 in the separation chamber or through screens 22 and 23 and hence through ports 17 or 18. A sample fraction scan can be made by varying Vc while the voltage gradient Eo should be maximized to obtain the highest separation performance. The eluent Qf from collection port 21 enters an ultraviolet detector and is displayed as a conventional histogram.

Thus, by varying the transverse focusing flow Vc against a constant electric field Eo, a scan of the fraction content of a sample can be made. This type of scan of a sample is unique in a separation device since the peak histogram is a function of the time rate of change of the focusing velocity Vc and is given by $\mu$=Vc/Eo. The time rate of change Vc is set by precision control of the purge valves 15 and 16. This allows real time control of the separation process. Continuous sample collection can be made by stopping the scan at a peak of interest, or made after the complete scan has been made by recovering the transverse velocity Vc corresponding to a peak of interest.

The peak values are detected by a liquid chromatography flow cell and detector system and fed back into the computer to achieve a feed-back control system. Cooling of the electrode chambers 4, 5 is provided by the electrode rinse flow while the purge flow Up provides cooling for the rest of the chamber. The flow velocity Up in the purge chambers 2, 3 may be up to ten times that in the separation chamber 1 in order to accomplish this purpose. The pore size of the screens 22, 23 is small (presently 0.005 cm hole, 50% open area) and thickness 0.5 mm. While the small holes will dampen disturbance flows between the separation chamber 1 and the purge chambers 2, 3, it is advisable to consider pressure drops in the separation and purge chambers so that $b_p^2/b_c^2$=Up/Uc where $b_p$ and $b_c$ are the thickness of the purge and separation chambers respectively. Confining the sample stream to the center region of the chamber avoids adsorption of the sample material on the containing "walls", screens 22 and 23. Evacuated glass side walls will preclude heat transfer in the lateral direction. This condition eliminates any variance in this direction so that scale-up of the sample stream width is unlimited.

Referring to FIG. 1, it can be seen that the injection port 6 is part of the chamber end wall. This configuration provides a simple means to manufacture very thin injection ports using spacer materials. Further, the carrier buffer flows from ports 7 and 8 converge at the sample injection port entrance to the chamber. This configuration is capable of producing injection lamina on the order of a micron. With $Q_s<<Q_{ci}$, an acceleration of the sample lamina occurs at the injection point caused by the converging buffer flows. Since continuity must be maintained, the sample lamina becomes thinner by the ratio of these flows. Thus, very thin lamina can be injected and collected instead of the usual cylindrical configurations.

II. Preparative Configuration

Figure 2:
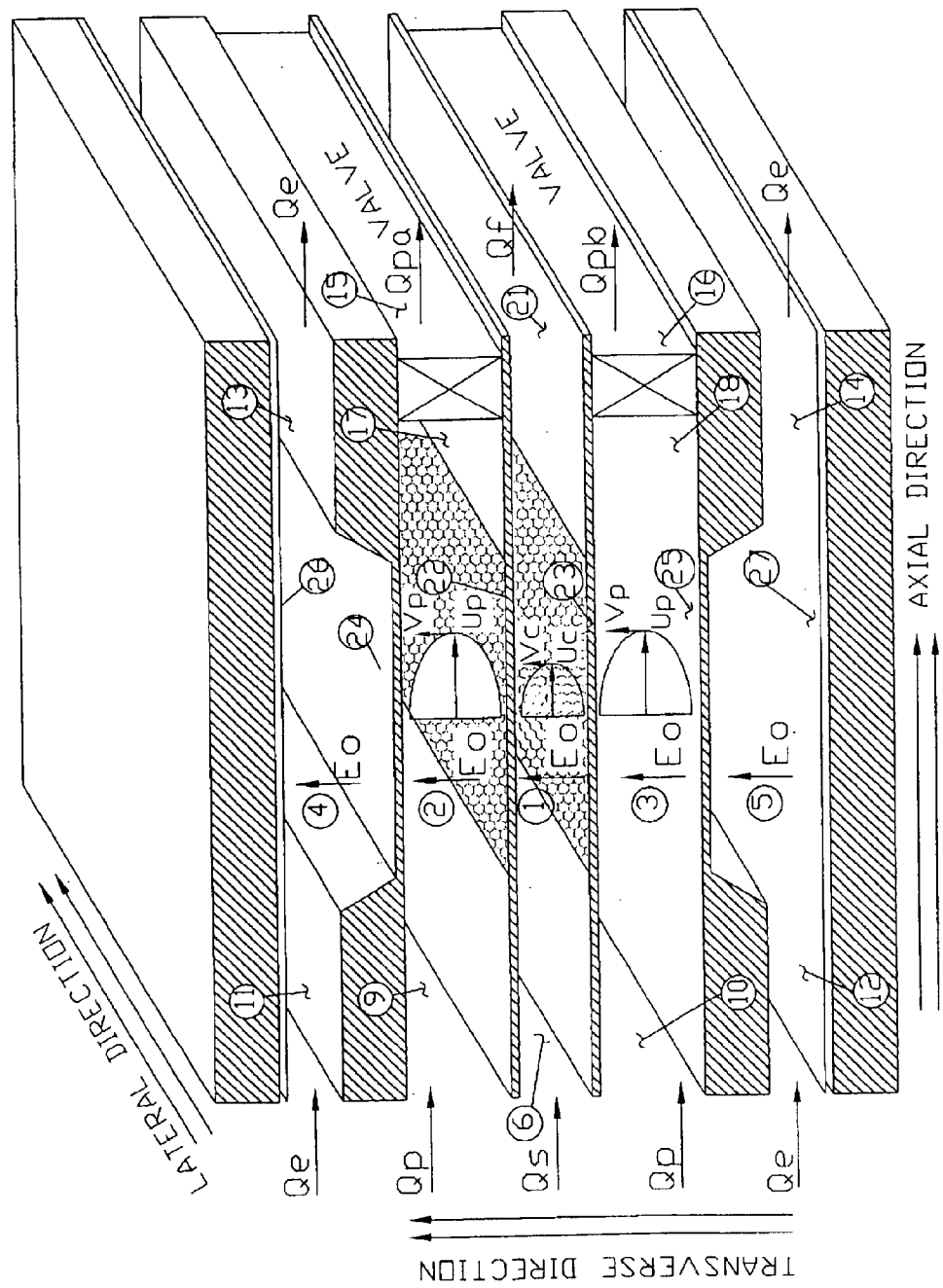
FIG. 2 is a schematic representation of the preparative configuration of the present invention, taken in the axial, transverse and lateral directions.

FIG. 2 shows the three-dimensional chamber in its preparative configuration with the different flows and flow regions. The chamber is comprised of a plurality of flow regions or sub-chambers, such as the five elements 1, 2, 3, 4 and 5. In the preferred embodiment, the separation chamber 1 is bounded by two fine mesh, precision pore, insulated screens 22 and 23. Carrier buffer enters the chamber mixed with the sample as Qs through port 6. The buffer and sample fill the entire separation chamber and flow through the chamber as shown. The focused sample fraction Qf exits the chamber through port 21.

As shown in FIG. 2, the separation chamber 1 is flanked by two purge chambers 2 and 3. The purge flows Qp enter through ports 9 and 10 and cause a velocity profile Up in the purge chambers. The purge flows exit through ports 17 and 18 and through purge valve A, 15 and purge valve B, 16. The relative purge valve openings set the purge flow out Qpa and Qpb and thus regulate the amount of cross-flow in the separation chamber. An electric field Eo is impressed in the separation chamber 1 by electrodes 26 and 27. These electrodes are located in the electrode chambers 4 and 5, respectively. Rinse flows Qe enter the chamber through ports 11 and 12 to expel electrolysis products through ports 13 and 14. Membranes 24 and 25 isolate the electrode chambers from electrolysis gas and products while allowing current flow to maintain the electric field.

If the upper electrode 26 is negative and the bottom electrode is positive, an electric field Eo exists in the separation chamber 1 which will cause a negatively charged sample to migrate down (negative transverse direction) against the uniform transverse focusing velocity Vc as determined by the relative settings of the purge valves 15 and 16. Consider a sample fraction of electrophoretic mobility $\mu_i$=Vc/Eo that has been injected through the injection port 6 located at the separation chamber center plane. The sample fraction $\mu_i$ will remain in the separation chamber 1 and move through it with the carrier buffer flow and be collected at the collection port 21. All other sample (mobility different than $\mu_i$) will exit the separation chamber through screens 22 and 23 and hence through ports 17 or 18. A sample fraction scan can be made by varying Vc while the voltage gradient Eo should be maximized to obtain the highest separation performance. The eluent Qf from collection port 21 enters an ultraviolet detector and is displayed as a conventional histogram.

Thus, by varying the transverse focusing flow Vc against a constant electric field Eo, a scan of the fraction content of a sample can be made. This type of scan of a sample is unique in a separation device since the peak histogram is a function of the time rate of change of the focusing velocity Vc and is given by $\mu$=Vc/Eo. The time rate of change Vc is set by precision control of the purge valves 15 and 16. This allows real time control of the separation process. Continuous sample collection can be made by stopping the scan at a peak of interest, or made after the complete scan has been made by recovering the transverse velocity Vc corresponding to a peak of interest.

The peak values are detected by a liquid chromatography flow cell and detector system and fed back into the computer to achieve a feed-back control system. Cooling of the electrode chambers 4, 5 is provided by the electrode rinse flow while the purge flow Up provides cooling for the rest of the chamber. The flow velocity Up in the purge chambers 2, 3 may be up to ten times that in the separation chamber 1 in order to accomplish this purpose. The pore size of the screens 22, 23 is small (presently 0.005 cm hole, 50% open area) and thickness 0.5 mm. While the small holes will dampen disturbance flows between the separation chamber 1 and the purge chambers 2, 3, it is advisable to consider pressure drops in the separation and purge chambers so that so that $b_p^2/b_c^2$=Up/Uc where $b_p$ and $b_c$ are the thickness of the purge and separation chambers respectively. Confining the sample stream to the center region of the chamber avoids adsorption of the sample material on the containing "walls", screens 22 and 23. Evacuated glass side walls will preclude heat transfer in the lateral direction. This condition eliminates any variance in this direction so that scale-up of the sample stream width is unlimited.

In order to use electrophoretic focusing for high resolution separations, the cross-flow must be essentially constant along both axial and transverse directions. For example, when purge valve A is open more than purge valve B, there is a net flow from the lower purge chamber 3 through the separation chamber 1 and into the purge chamber 2. It is the transverse component of this flow velocity in the separation chamber which constitutes the focusing cross-flow. To assure that this cross-flow is constant in the axial direction, the flows and chamber dimensions must be carefully designed. Solving second order differential flow equations for the total flow system shows that indeed the cross-flow does not significantly change axially if the chamber geometry and operating parameters are selected so that the transverse flow resistance in the screen is much larger than the axial flow resistance in the purge chambers.

Considering the plurality of flows necessary for operation, it is obvious that a simple and effective method of flow control must be devised. Since the pressure drops in the chamber are on the order of 1 Newton per meter squared, it would require an expensive and complicated method of control by pressure measurement and feedback. The problem is solved through the use of high resistance flow restrictors in the entrance and exit flow regions, allowing flow to be supplied by a single pump for each purpose. A lumped flow resistance model was developed for the electrophoretic focusing chamber. If the entrance flow restrictors have a much greater flow resistance than the chamber components, then the flow will be equally split into each purge chamber and no measurement or control system is necessary. This configuration was also used to split the entrance and exit carrier buffer flows. The electrode rinse flows are not synchronized or controlled but only set at a sufficient magnitude to remove the electrolysis products.

As the Figures show, the temperature gradient that affects the sample mobility is co-directional with the sample migration. This is in contrast to zonal techniques such as CE and CFE where the temperature gradients are perpendicular to the sample migration. When the electrophoretic migration and temperature gradient are co-directional as they are in electrophoretic focusing, it can be shown that the temperature-induced mobility dispersion is compensated by the temperature-induced variations in buffer dielectric constant and buffer electrical resistivity. Taking the variations of mobility, buffer dielectric constant and resistivity from experimental data, the classic mobility equation (Smoluchowski) can be solved as a function of temperature. The results show that any temperature-induced mobility dispersion is compensated by the temperature-induced buffer properties and thus does not vary significantly over a temperature range from 0° C. to 40° C.

The referenced publication by Rhodes, et al., 1989, predicts that a thin ribbon or lamina is the most stable sample configuration against the electrohydrodynamic distortion that occurs when the sample stream introduces a conductivity perturbation in the flowing buffer. Recently, it was found that electrohydrodynamic disturbances are minimized when the separation chamber is completely full of sample or when the sample lamina are very thin. These conclusions were demonstrated experimentally and have been verified using numerical analysis. Using this effect in the chamber design, numerical analysis has shown that the very thin sample streams produce electrohydrodynamic flows two orders of magnitude less that electrophoretic migration velocities. For the preparative configuration, the separation chamber can be filled with sample. This will reduce the conductivity variation in the separation chamber and produce equal attenuation of the electrohydrodynamic flow.

The above description presents only illustrative embodiments of the present invention, and it will be clear to one skilled in this art that additional alternative embodiments not set forth above will fall within the scope of the invention.

The following example is present only as illustrative of the present invention, the scope of which is defined by the claims appended hereto, and thus is not intended to limit the invention in any manner.

EXAMPLE

Prototype instruments in accordance with the present invention were built and tested as set forth in the descriptions given above. Dye materials, methyl orange and coomassie blue, were mixed with a phosphate buffer to test the deflections according to electrophoretic mobility and focusing cross-flow. After stabilizing the mixture stream by adjustments of the pumps and valves, the electric field was applied resulting in the deflection of the various colored components out of the separation chamber, through the screens into the purge chambers. The introduction of the appropriate cross-flow brought all sample streams back to a condition such that the lowest mobility yellow dye entered the "left" purge chamber, intermediate dye, red, focused in the central separation chamber and the highest mobility dye, blue, remained deflected in the "right" purge chamber. These separations were shown to be stable and repeatable.

What is claimed is:

1. A method for separation and collection of at least one sample component from a mixture of sample components comprising the steps of:
    a. providing an apparatus comprising a separation chamber and a plurality of purge chambers and purge valve, and establishing a first buffer flow in the separation chamber in the axial direction, said first buffer flow having a first flow rate;
    b. establishing a second buffer flow in the separation chamber consisting of two flows on either side of the first flow that converge on the first flow at the separation chamber flow entrance and diverge from the first flow at the separation chamber flow exit;
    c. establishing a third buffer flow in each of at least two purge chambers;
    d. introducing two precision-pore screens that partition the said separation chamber from each of the at least two said purge chambers;
    e. establishing a fourth buffer flow by the biasing of the purge valves to control said fourth buffer flow from one of the purge chambers in the axial direction through a precision-pore screen transversely into the separation chamber, then out of the separation chamber through the second precision-pore screen into a second purge chamber, thus providing the required uniform focusing fluid velocity in the separation chamber;
    f. introducing the mixture of sample components with the said first buffer flow directly into the separation chamber flow entrance or through at least one injection port located in the separation chamber interior;
    g. controlling the second buffer flow to converge and thin the first buffer flow with the mixture of sample components at the separation chamber entrance and then diverge and extract fractional sample components from the mixture of sample components at the separation chamber exit; and
    h. applying an electrical potential transversely across the separation chamber in the form of a constant voltage gradient to impart electrophoretic velocity to the fractional sample components in the separation chamber in the transverse direction perpendicular to the first buffer flow direction and parallel to the fourth buffer flow direction.

2. A method according to claim 1 wherein the sample components are extracted through a single collection port or from each of a plurality of collection ports.

3. A method according to claim 1 wherein the sample components are injected with the said first flow at the separation chamber flow entrance and thinned by said second buffer converging co-flow.

4. A method according to claim 1 wherein one sample component is maintained in the separation chamber while extraneous components are discarded with the said third flow through the purge chambers and discarded with the diverging said second flow at the exit of the separation chamber.

5. A method according to claim 4 wherein the extraneous components being withdrawn may be recycled and reinjected back into the separation chamber to minimize any loss of valuable sample constituents.

6. A method according to claim 1 wherein the said fourth buffer flow is adjusted by manipulation of said purge valves to provide a transversely varying cross-flow velocity which allows any selected sample component to be either analyzed or collected at a single collection port.

7. A method according to claim 6 wherein the sample is acted on by the combined influences of a constant electric field and said fourth buffer flow transversely across the separation chamber.

8. A method according to claim 6 wherein the selected sample component is collected at the flow exit of the separation chamber.

9. A method according to claim 1 wherein at least one fractional sample component is maintained in the separation chamber and arrives at a single collection port in the separation chamber while extraneous components are either discarded through the said purge chambers or flow around the collection port and out of the separation chamber at the carrier buffer flow exit.

10. A method according to claim 9 wherein at least one fractional sample component may be scanned in the exit region of the separation chamber by a detector system with at least one fractional sample component being collected in a single or multiple set of collection ports.

11. A method according to claim 9 wherein a spectrum of the fractional sample components may be analyzed or collected by varying the flow of pump in a linear variation to present a time-dependent histogram.

12. A method according to claim 1 wherein a spectrum of the fractional sample components in the separation chamber completely fills the transverse chamber thickness with the remainder of the spectrum being diverted through said precision-pore screens into and out of the purge chambers.

13. A method according to claim 12 wherein the spectrum being viewed may be changed by varying the control of said purge valves.

14. A method according to claim 12 wherein the spectrum being viewed may be collected in at least one single collection port by varying the purge valve settings for the fourth flow rate of focusing fluid velocity.

* * * * *